United States Patent [19]

Bentley

[11] 4,062,360
[45] Dec. 13, 1977

[54] ATRAUMATIC FLUID HANDLING METHOD AND APPARATUS

[75] Inventor: Donald J. Bentley, Irvine, Calif.

[73] Assignee: Bentley Laboratories, Inc., Irvine, Calif.

[21] Appl. No.: 672,982

[22] Filed: Apr. 2, 1976

[51] Int. Cl.² .............................................. A61M 1/00
[52] U.S. Cl. ................................ 128/276; 128/214 B; 128/DIG. 3
[58] Field of Search ............... 128/297, 214 R, 214 B, 128/DIG. 3, 276–278, ; 23/258.5 R, 258.5 A; 137/205, 110, 510, 801, 485; 251/5, 63, 12, 282, 331

[56] References Cited

U.S. PATENT DOCUMENTS

| | | | |
|---|---|---|---|
| 2,927,582 | 3/1960 | Berkman et al. | 128/DIG. 3 |
| 3,469,582 | 9/1969 | Jackson | 128/276 |
| 3,763,862 | 10/1973 | Spieth | 128/276 |
| 3,799,702 | 3/1974 | Weishaar | 128/278 |
| 3,907,504 | 9/1975 | Hammond et al. | 23/258.5 |
| 3,918,453 | 11/1975 | Leonard | 128/278 |
| 3,932,065 | 1/1976 | Ginsberg et al. | 251/5 |
| 3,965,896 | 6/1976 | Swank | 128/276 |
| 3,968,795 | 7/1976 | O'Neill et al. | 128/142.3 |

Primary Examiner—Ronald L. Frinks
Assistant Examiner—Henry S. Layton
Attorney, Agent, or Firm—Lyon & Lyon

[57] ABSTRACT

An atraumatic method and apparatus for the removal of fluid from a surgical field having a fluid valve which is opened and closed responsive to the pressure about the fluid valve and a vacuum valve which is also opened and closed in response to the pressure about the fluid valve, and when opened, causes fluid to be passed through the fluid valve. In one embodiment, the fluid valve is made of collapsible tubing, flattened at its midsection so as to be normally closed, and connecting a fluid inlet and fluid outlet of a fluid removal housing. The fluid removal housing is further provided with a control port which may be opened or closed manually, and a connection to a vacuum source through the vacuum valve.

22 Claims, 5 Drawing Figures

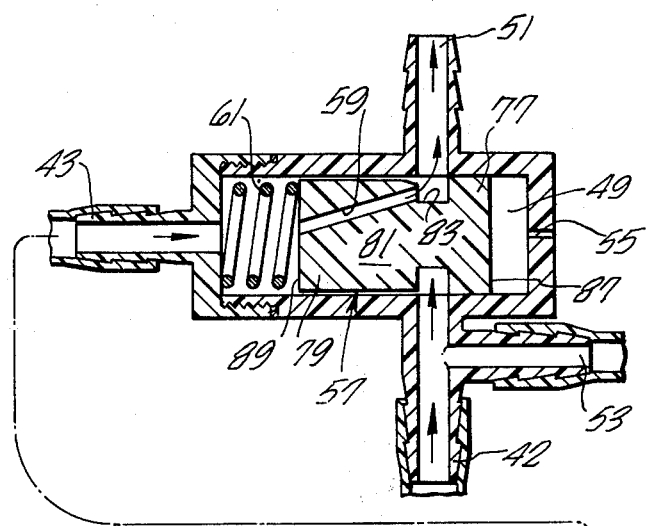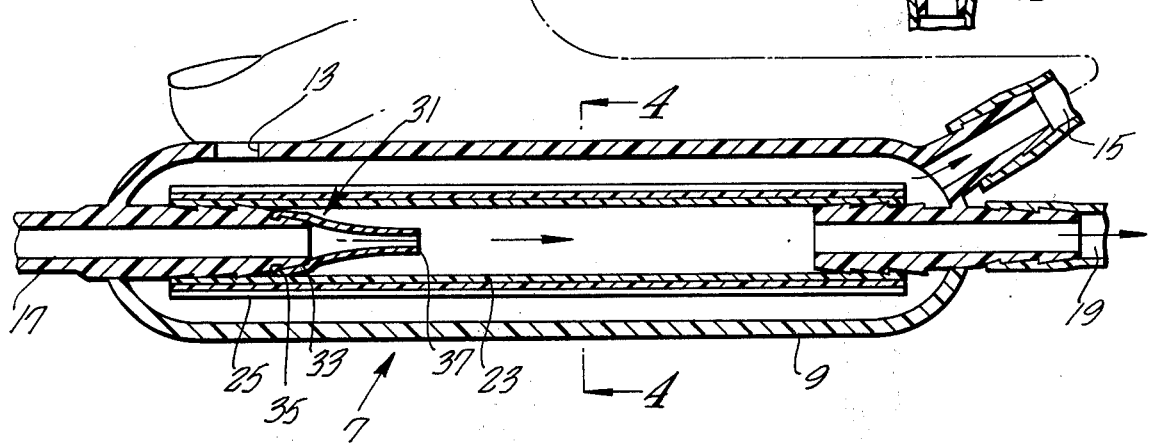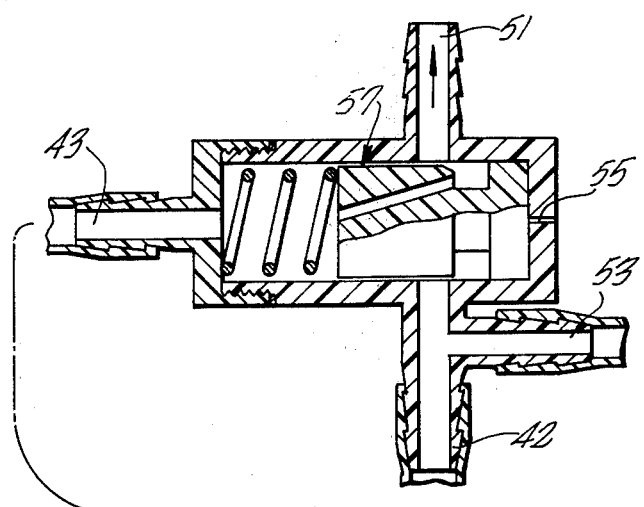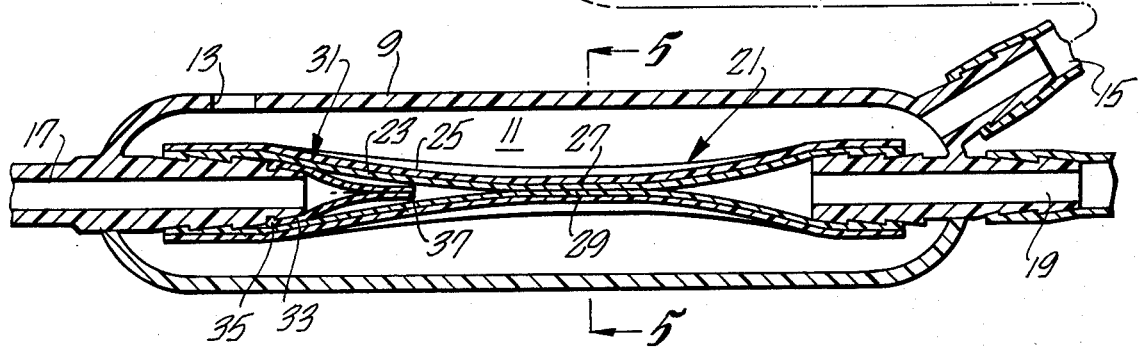

ATRAUMATIC FLUID HANDLING METHOD AND APPARATUS

BACKGROUND OF THE INVENTION

1. Field of the Invention

The invention relates to a method and apparatus of atraumatic fluid removal. More particularly, it relates to an improved method and apparatus for the removal of body fluids from a surgical field.

2. Brief Description of the Prior Art

During many types of surgery where there is a large blood loss, it is necessary to aspirate the blood from the incision in order to provide visibility for the surgeon, and it is desirable to return the aspirated blood to the patient. This is particularly true during open heart surgery where the pericardium is cut and the total flow from the coronary arteries must be aspirated in order to be returned to the patient.

One of the major sources of damage to the red cells during open heart and other surgeries where major blood losses occur, is caused by the procedure utilized to aspirate the blood from the wound and return it to the patient. A significant portion of this blood damage or trauma is a result of the technique used by the surgeon handling the blood removal instrument, that is, allowing the blood to pool and removing the blood from the pool with the instrument is less traumatic to the blood than sucking the blood from the surface of the tissues. The other major source of trauma to the blood during this procedure is due to the functioning of the system itself, that is, suction is provided by connecting, typically with tubing, the blood removal device to a standard, peristolic pump which provides the suction and forces the blood through a cardiotomy reservoir, from which it may flow by gravity to an oxygenator and return to the patient. For a more complete description of the operation of a cardiotomy reservoir and a blood oxygenator see my U.S. Pat. No. 3,507,395 hereby incorporated by reference.

Since it is necessary to retain the surgical field "dry", in order to maintain sufficient visibility, the pump is allowed to run all the time whether or not it is pumping blood. The major portion of the time the pump is pumping a small amount of blood with a large amount of gas, and the blood that remains in the lines is agitated repeatedly before it is sucked through a roller pump in the cardiotomy reservoir.

There are systems in which a switch is provided to the surgeon, who either shuts off the roller pump when the sucker is not in use, or in some cases switches to a lower speed for the roller pump during that period. This system is unsatisfactory for two reasons. First, the surgeon must remember to actuate the switch, which is done usually with his foot; and second, even if he actuates the switch, if the pump is shut off then the residual blood in lines can and frequently does leak from the lines back into the field, obscuring the surgeon's vision.

It is an object of this invention to provide an improved apparatus and method for the atraumatic removal of body fluids from a surgical field. Other and additional objectives will become apparent upon reading of the entire specification, drawings and claims.

SUMMARY OF THE INVENTION

A method and apparatus for atraumatic removal of fluid from a location such as a surgical field is provided by this invention. A fluid valve is opened and closed responsive to the pressure about the valve, similarly a vacuum valve is opened and closed responsive to pressure about the fluid valve. The fluid valve may comprise a collapsible tubing, flattened at its midportion, and connecting an inlet and an outlet of a fluid removal housing within which the fluid valve is positioned. The tubing may be comprised of a first tube about which is positioned a second tube having a larger diameter than the first tube and attached to the first tube at at least one point. As the first and second tubes are both flattened at their midpoints, the fluid removal valve is normally closed. The fluid removal housing may also be provided with a control port and a vacuum inlet which may in turn be connected to a vacuum source through a vacuum control valve.

When the control port is closed, the vacuum source may be allowed to lower the pressure within the fluid removal housing thereby decreasing the pressure about the fluid removal valve. Simultaneously, the vacuum control valve may reduce the pressure at the fluid removal housing inlet thereby inducing the flow of fluid through the fluid valve. The fluid removal valve is caused to open as the force produced by the vacuum on the second outer tubing is greater than the force produced by the vacuum within the smaller first inner tubing, due to the larger surface area of the second or outer tubing upon which the vacuum acts.

The vacuum control means or valve may comprise a vacuum valve body forming a cavity which is in communication with a vacuum inlet connected to the vacuum source and first and second vacuum valve outlets. A valve closure means capable of closing the vacuum inlet may be positioned between the first vacuum valve outlet and a vent from the vacuum valve body to the amosphere. Further, a restricted passage may be provided between the vacuum valve inlet and the first vacuum valve outlet. As the control port of the fluid removal housing and the fluid removal housing vacuum inlet are in communication, and the fluid removal housing vacuum outlet is connected to the vacuum valve first outlet, when the control port is opened to the atmosphere, each side of the vacuum control valve closure means is exposed to the same pressure. When the control port is closed, the vacuum source lowers the pressure at the vacuum valve first outlet by means of flow through the restricted passage of the vacuum valve, and a differential pressure is thus applied across the vacuum valve closure means. The vacuum valve closure means may be adapted to be positioned in one of two predetermined positions, the first position blocking the vacuum valve inlet and the second position allowing communication between the vacuum valve inlet and the second vacuum valve outlet. The vacuum valve may be further provided with biasing means which urges the vacuum valve closure means toward the first or valve closure means position, and the differential pressure across the closure means will be utilized to urge the valve closure means into the second valve closure means position.

The control port may be manually operated, and in a preferred embodiment may be of such size that it may be occluded by the finger of the surgeon operating the fluid removal instrument. As is set out in the preceding description of the invention, this allows both for the opening of the fluid control valve and the removal of fluid through the valve.

BRIEF DESCRIPTION OF THE DRAWINGS

FIGS. 2 and 3 are cross sectional views illustrating the fluid removal housing and the vacuum control valve of this invention.

DESCRIPTION OF PREFERRED EMBODIMENTS

Figure 1:
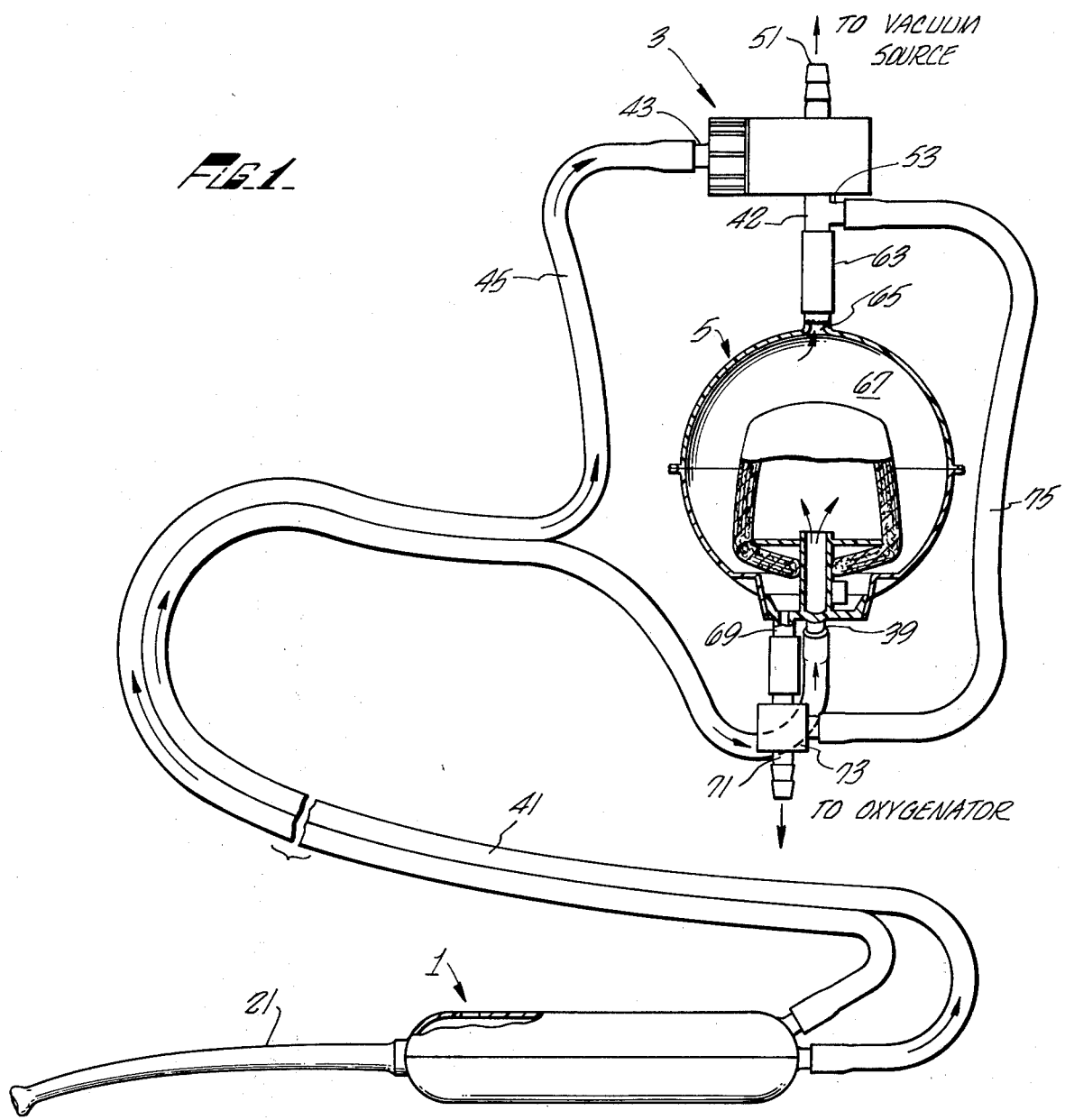
FIG. 1 is a pictorial view illustrating the apparatus of this invention.

Referring now to FIG. 1, a fluid removal instrument referred to generally as 1, a vacuum valving means generally referred to as 3, and a fluid reservoir generally referred to as 5 are shown. FIGS. 2 and 3 illustrate cross sectional views of the vacuum valving means 3 and a fluid valving means 7 which are a portion of the fluid removal instrument 1. Fluid valving means 7 will now be described in detail by means of reference to FIGS. 2 and 3.

A fluid removal housing 9 encloses a cavity 11 therein. The cavity 11 within the fluid removal housing 9 allows for the communication between a control port 13 and a vacuum inlet 15. The fluid removal housing is further provided with a fluid inlet 17 and a fluid outlet 19. The fluid inlet may be connected to a fluid removal probe portion 20 of the fluid removal instrument 1 which is shown in FIG. 1. A fluid valve, referred to generally as 21 is disposed within cavity 11 of the fluid removal housing 9 and connects fluid removal housing fluid inlet 17 and fluid removal housing fluid outlet 19. The fluid removal valve may be comprised of a first tube 23 about which may be positioned a second tube 25. The first tube 23 and the second tube 25 are shown more clearly in FIGS. 4 and 5 which illustrate the fluid valve 21 in the opened and closed positions respectively.

Figure 5:
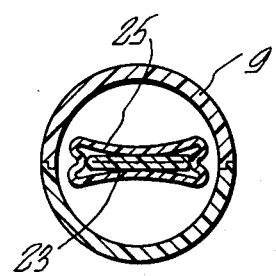

The midportion 27 of the first tube 23 and the midportion 29 of the second tube 25 may be flattened thereby allowing the fluid valve 21 to normally assume the closed position as is shown in FIGS. 3 and 5. The fluid valve 21 may be further provided with a check valve, referred to generally as 31. The check valve 31 may be comprised of a tubing section 33 having one end 35 joined to the fluid inlet 17 and the other end 37 being disposed within the first tube 23. The end portion 37 of the check valve 31 may be flattened so that it also normally assumes the closed position as is shown in FIG. 3.

Referring now to FIG. 1, the fluid outlet 19 of the fluid removal housing 9 may be connected to a reservoir 5 inlet 39 by means of a tubing 41. Similarly, the vacuum inlet 15 of the fluid removal housing 9 may be connected to a first outlet 43 of the vacuum valving means 3 by means of tubing 45. The vacuum valving means 3 will now be described in detail, making reference to FIGS. 2 and 3.

The vacuum valving means 3 may comprise a vacuum valve body 47 which defines a cavity 49 therein. The vacuum valving means or vacuum valve 3 may also be provided with a vacuum inlet 51 which may be connected to a vacuum source (not shown), a first outlet 43 and a second outlet 42. In a preferred embodiment, which will be described in detail later when a method of operation of the apparatus of this invention is described, a branch connection 53 may be provided in communication with the vacuum valving means second outlet 42. The vacuum valving means 3 is further provided with a vent 55 which may be opened to the atmosphere. Located between the vent 55 and the first outlet 43 of the vacuum valve 3 may be positioned a closure means 57. The closure means 57 of the vacuum valve 3 may be adapted to be positioned in one of two predetermined positions. The first position is illustrated in FIG. 3 where the closure means 57 is shown to substantially block the vacuum inlet 51 and the second outlet 52 of the vacuum valve. The second position, or open position of the vacuum valve closure means 57 is illustrated in FIG. 2 wherein the vacuum inlet 51 and the second outlet 42 of the vacuum valve 3 are in communication. A restricted passage such as 59 may be provided joining the vacuum source and the first outlet 43 of the vacuum valve 3. Additionally, a biasing means 61, urging said vacuum valve closure means 57 to assume the first position illustrated in FIG. 3 may also be provided.

Referring now again to FIG. 1, the interrelationship of the fluid removal instrument 1, the vacuum valving means 3 and the reservoir 5 will be discussed. The second outlet 42 of the vacuum valve 3 may be connected by means of a connector 63 to a vacuum inlet 65 of the reservoir 5 so as to allow the interior portion 67 of the reservoir 5 to be placed under a vacuum when the vacuum valve is in the open position as shown in FIG. 2. The reservoir 5 may be further provided with a fluid outlet 69 which may be connected by means of a connector 71 to an oxygenator (not shown). The connector 71 may be further provided with a check valve 73 which prevents reverse flow from the oxygenator back into the reservoir 5. In a preferred embodiment, the check valve 73 is a vacuum actuated clamp which is actuated by means of a connector 75 which is in turn connected to the second outlet 42 of the vacuum valve 3 by means of the branch connection 53.

Having defined the apparatus of the instant invention in detail, its method of operation will now be discussed. When the surgeon who is operating the fluid removal instrument 1 desires to remove fluid from the surgical field he may occlude the control port 13 by manually placing his finger or hand over the port. When this is done, the vacuum source lowers the pressure at the first outlet 43 of the vacuum valve 3 and the pressure of the cavity 11 of the fluid removal housing 9. This causes two things to happen substantially simultaneously.

A differential pressure builds across the closure means 57 of the vacuum valve 3. This is due to the fact that the pressure exerted at a first face 87 of the closure means 57 remains constant as there is no change in the pressure exerted on this portion of the closure means 57 due to the vent 55 which is open to the atmosphere. However, the opposite face 89 is now exposed to decreasing pressure due to the fact that the pressure at the location of the first outlet 43 is reduced by means of flow through the restricted passage 59.

The valve closure means 57 may be further defined as comprising a spool body 81 having a first head member 77, a second head member 79 and a connective member 83, the diameter of the connective member 83 being less than that of head members 77 and 79. The head members 77 and 79 are adapted to slide from the first position shown in FIG. 3 to the second position shown in FIG. 2. When the closure means 57 is in the closed position as is illustrated in FIG. 3, the second head member 79 blocks the vacuum inlet 51 and the second outlet 42 of the vacuum valve 3. When the valve closure means 57 is in the open position, the neck portion 83 of the valve closure body 81 is positioned adjacent the vacuum inlet 51 and the second outlet 42 of the vacuum valve 3 thereby allowing for flow about the neck member 83.

As the pressure decreases at the first outlet 43 of the vacuum valve 3, the force exerted upon the closure means body 81 along fact 79 decreases while the pressure exerted at face 77 remains constant, thus producing a differential across the closure means body 81 and urging the body to overcome the biasing means 61 and move the closure means 81 into the open position shown in FIG. 2 wherein the vacuum inlet 51 and the second outlet 42 of the vacuum valve 3 are in communication.

When the vacuum valve 3 is in the open position, the reservoir 5 is placed under vacuum by means of the connector 63, and the vacuum clamping means 73 is closed. Fluid is pulled through the probe member 20 of the fluid removal instrument 1 through the open fluid valve 21 and into the reservoir 5 through the connector tubing 41.

Figure 4:
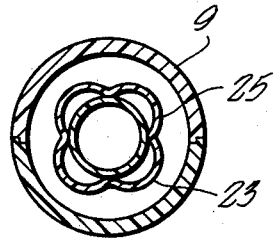
FIGS. 4 and 5 are cross sectional views taken about line 4—4 of FIG. 2 and line 5—5 of FIG. 3 respectively.

At substantially the same time the vacuum valve 3 is opening, the pressure in the cavity 11 of the fluid removing housing 9 is decreased as the cavity is connected to the vacuum first outlet 43 via vacuum inlet 15 and connector 43, and the force exerted on the second tube 25 is decreased. Such a decrease in pressure opens the second tube and the first tube attached thereto. Due to the larger area of the second tube 25 which is exposed to the reduced pressure, the fluid valve 21 will assume the open position as is shown in FIG. 4 even when both the first and second tubes 23 and 25 are exposed to the same reduced pressure by the vacuum source. Fluid flow through the fluid removal housing 9 forces the check valve 37 into the open position as is shown in FIG. 2.

Similarly, when the surgeon who is operating the fluid removal instrument desires to terminate the fluid removal operation he simply removes his finger from the control port 13 thereby opening the control port 13. Again, this causes two things to occur substantially simultaneously. As the pressure in the cavity 11 increases due to the exposure to the atmosphere through the open control port 13, the fluid valve 21 is forced into the closed position as is illustrated in FIG. 3. When flow ceases through the check valve 31, the check valve 31 assumes its normal closed position as is illustrated in FIG. 3, thus preventing any fluid from leading back into the surgical field.

Increased pressure is also communicated to the first outlet 43 of the vacuum valve 3 by means of the connector tubing 45 which connects the vacuum inlet 15 of the fluid removal housing 9 to the first outlet 43 of the vacuum valve 3. As the pressure at the first outlet 43 of the vacuum valve 3 approaches atmospheric pressure, the pressure on faces 89 and 87 equalize thereby neutralizing the opposing forces and allowing the biasing means 61 to force the closure means 57 into first or closed position illustrated in FIG. 3. As the reservoir is no longer in communication with the vacuum source as the second outlet 42 is no longer in communication with the vacuum source and the vacuum actuated clamp 73 is correspondingly deactivated, fluid may be allowed to flow from the reservoir to the oxygenator by gravity or other means.

It may be desirable to provide a plurality of fluid removal instruments 1 each being connected to the first outlet 43 of the vacuum valve 3. When it is desired to utilize two fluid removal instruments 1 at the same time, after the first fluid removal instrument is utilized by closing the control port 13 the second fluid removal instrument is brought into operation in the same manner.

Since no fluid passes through the control valve 3, the control valve 3 can be either disposable or reusable. If reusable, it is preferably made a part of the holder for the reservoir 5. In the embodiment in which it is a reusable item made a part of the holder for the reservoir 5, it is particularly advantageous to use the vacuum actuated clamp 73 on the outlet 69 of the reservoir 5, since the clamp can also be reusable.

In the embodiment in which it is desired to make the control valve a disposable item, the reservoir 5 is preferably supplied with a disposable one way check valve such as check valve 31. It is also desirable that the fluid removal instrument tip 20 and housing 9 be disposable items since fluid is drawn through the members and cleaning for reuse may be impractical.

Although preferred embodiments of the invention have been described, it will be readily apparent that alteration and modification may be resorted to without departing from the scope of this invention, and such alterations and modifications are intended to be included within the scope of the appended claims.

I claim:

1. An atraumatic method of fluid handling comprising:
   opening a fluid valve responsive to the pressure decrease about said fluid valve;
   opening a vacuum valve responsive to the pressure decrease about said fluid valve; and
   conveying fluid through said fluid valve response to said opening of said vacuum valve.

2. The atraumatic method of fluid handling claimed in claim 1 wherein said method is further described as comprising:
   biasing said fluid valve and said vacuum valve to assume a normally closed position.

3. The atraumatic method of fluid handling claimed in claim 1 wherein said method is further defined as comprising:
   transferring said conveyed fluid from said fluid valve to a fluid reservoir.

4. The atraumatic method of fluid handling claimed in claim 1 wherein said method is further defined as comprising:
   oxygenating said fluid.

5. An atraumatic method of fluid handling comprising:
   biasing a fluid valve and a vacuum valve to a normally closed position;
   opening said vacuum valve responsive to a pressure decrease about said fluid valve;
   opening said fluid valve responsive to the pressure decrease about said fluid valve; and
   conveying fluid through said fluid valve responsive to said opening of said vacuum valve.

6. The atraumatic method of fluid handling claimed in claim 5 wherein said method further comprises:
   transferring said fluid from said fluid valve to a fluid reservoir.

7. The atraumatic method of fluid handling claimed in claim 5 wherein said method further comprises:
   oxygenating said fluid.

8. A fluid removal means comprising:
   a fluid removal housing defining a cavity, said cavity being in communication with a vacuum inlet and a control port, and said fluid removal housing having a fluid inlet and a fluid outlet;

connective means adapted to join a vacuum source and said fluid removal housing vacuum inlet and said fluid outlet; and fluid valving means located within said fluid removal housing cavity, said valving means including a first collapsible tube joining said fluid inlet and outlet and a second collapsible tube surrounding said first tube; said second collapsible tube being connected to said first collapsible tube and said second collapsible tube having a larger surface area than said first collapsible tube.

9. The fluid removal means claimed in claim 8 wherein said second collapsible tube of said fluid valving means is further defined as having a diameter which is substantially larger than the diameter of said first collapsible tube.

10. The fluid removal means claimed in claim 8 wherein said fluid valving means further comprises a check valve within said first collapsible tube adapted so as to prevent fluid flow from said fluid outlet to said fluid inlet.

11. The fluid removal means claimed in claim 10 wherein said check valve is further defined as comprising a section of tubing positioned within said first tube and having one end connected to said fluid removal housing fluid inlet, said tubing section being further defined as having that portion opposite said end connected to said fluid removal housing fluid inlet flattened so that said check valve is normally closed thereby preventing fluid from passing from said fluid removal housing outward through said fluid inlet.

12. The fluid removal means claimed in claim 8 wherein said first and second tubes are further defined as being flattened at the center portion of their length so that said first and second tubes are normally closed thereby preventing the flow of fluid therethrough.

13. A fluid removal system comprising:
a vacuum source;
a fluid removal housing defining a cavity, said cavity being in communication with a vacuum inlet and a control port, and said fluid removal housing having a fluid inlet and a fluid outlet;
conductive means joining said vacuum source and said fluid removal housing vacuum inlet and said fluid outlet; and
fluid valving means located within said fluid removal housing, said valving means including a first collapsible tube joining said fluid inlet and said fluid outlet, a second collapsible tube having a diameter and surface area substantially larger than said first tube said second tube surrounding said first tube and being attached to said first tube at at least one point; and
a check valve positioned within said first collapsible tube adapted to prevent fluid flow from said fluid outlet to said fluid inlet.

14. A fluid removal system comprising:
a vacuum source;
a fluid removal housing defining a cavity said cavity being in communication with a vacuum inlet and a control port and said fluid removal housing having a fluid inlet and a fluid outlet;
fluid valving means located within said fluid removal housing cavity, said valving means including a first collapsible tube joining said fluid inlet and outlet and a second collapsible tube surrounding said first tube;
vacuum valving means;
connective means joining a vacuum source to said vacuum valving means; and
connective means joining said vacuum valving means to said fluid removal housing inlet and said fluid outlet,
said vacuum valving means being connected to said vacuum source and to said fluid removal housing inlet and said fluid outlet being responsive to the pressure about said fluid valving means.

15. The fluid removal system claimed in claim 14 wherein said vacuum valving means is further defined as comprising a:
vacuum valve body forming a cavity therein;
a vacuum valve inlet and a first vacuum valve outlet in communication with said fluid removal housing vacuum inlet and a vacuum valve second outlet in communication with said fluid removal housing fluid outlet;
a valve closure means having biasing means adjacent thereto to substantially close said vacuum valve inlet and said second vacuum valve outlet; and
control means adapted to overcome said valve closure biasing means whereby said vacuum source is opened to said fluid removal housing fluid outlet and said vacuum inlet thereby opening said first and second tubes and allowing fluid to flow therethrough.

16. The fluid removal system claimed in claim 15 wherein said vacuum valving means is further defined as having said valve closure means positioned between said first vacuum valve outlet and a vent from said vacuum valve body to the atmosphere, and restricted passage means are provided between said vacuum valve inlet and said first vacuum valve outlet, thereby allowing for the equalization of pressures on either side of said closure means when said first vacuum valve outlet is in communication with the atmosphere, and allowing for the application of a pressure differential across said closure means when said first vacuum outlet is isolated from the atmosphere and the pressure at said first vacuum valve outlet is decreased by flow through said restricted passage means.

17. The fluid removal system claimed in claim 16 wherein said vacuum valving means is further defined as providing a valve closure means adapted to be positioned in one of two predetermined positions, said first position substantially blocking said vacuum valve inlet and said second vacuum outlet, and said second position allowing communication between said vacuum valve inlet and said second vacuum valve outlet.

18. The fluid removal system claimed in claim 17 wherein said biasing means urges said closure means toward said first valve closure means position and said differential pressure across said closure means urges said closure means toward said second valve closure means position.

19. The fluid removal system claimed in claim 15 wherein a reservoir is provided having a fluid inlet connected to said fluid removal housing fluid outlet and a vacuum inlet connected to said second vacuum valve outlet whereby fluid removed through said fluid removal housing is drawn into said reservoir.

20. The fluid removal system claimed in claim 19 wherein said reservoir is connected to an oxygenator, whereby fluid removed through said fluid removal housing is drawn through said reservoir and then passed to said oxygenator.

21. The fluid removal system claimed in claim 20 wherein means are provided to prevent flow in said reservoir-oxygenator connection from said oxygenator into said reservoir.

22. The fluid removal system claimed in claim 21 wherein said means to prevent flow from said oxygenator into said reservoir is further defined as comprising a vacuum activated clamping means positioned about the reservoir-oxygenator connection, said clamping means being in communication with said second vacuum valve outlet whereby said clamping means is only activated when said reservoir is under vacuum.

* * * * *